United States Patent
Mertens et al.

(10) Patent No.: US 6,911,038 B2
(45) Date of Patent: Jun. 28, 2005

(54) MATCHED BALLOON TO STENT SHORTENING

(75) Inventors: Steven P. Mertens, New Hope, MN (US); Fernando DiCaprio, Mendota Heights, MN (US); Brian Brown, Hanover, MN (US); Lixiao Wang, Long Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/850,815

(22) Filed: May 8, 2001

(65) Prior Publication Data

US 2002/0169494 A1 Nov. 14, 2002

(51) Int. Cl.[7] .............................. A61F 2/06; A61M 29/00
(52) U.S. Cl. ........................................ 623/1.11; 606/192
(58) Field of Search ................................ 623/1.11, 1.13, 623/1.44, 194; 606/198, 192, 108, 191, 194, 96.01, 104; 604/96.01, 103.05, 103.06

(56) References Cited

U.S. PATENT DOCUMENTS

| | | | | |
|---|---|---|---|---|
| 4,364,392 A | | 12/1982 | Strother et al. | 128/325 |
| 5,108,370 A | | 4/1992 | Walinsky | 604/96 |
| 5,338,299 A | | 8/1994 | Barlow | 604/96 |
| 5,409,495 A | * | 4/1995 | Osborn | 606/108 |
| 5,456,667 A | | 10/1995 | Ham et al. | 604/107 |
| 5,470,314 A | | 11/1995 | Walinsky | 604/96 |
| 5,500,181 A | | 3/1996 | Wang et al. | 264/532 |
| 5,634,936 A | * | 6/1997 | Linden et al. | 606/213 |
| 5,690,643 A | * | 11/1997 | Wijay | 606/108 |
| 5,700,242 A | | 12/1997 | Mulder | 604/94 |
| 5,772,669 A | | 6/1998 | Vrba | 606/108 |
| 5,776,141 A | * | 7/1998 | Klein et al. | 606/108 |
| 5,788,626 A | * | 8/1998 | Thompson | 600/36 |
| 5,830,182 A | | 11/1998 | Wang et al. | 604/96 |
| 5,972,018 A | | 10/1999 | Israel et al. | 606/198 |
| 5,980,531 A | * | 11/1999 | Goodin et al. | 623/1.11 |
| 6,036,697 A | | 3/2000 | DiCaprio | 606/108 |
| 6,039,721 A | | 3/2000 | Johnson et al. | 604/508 |
| 6,117,168 A | * | 9/2000 | Yang et al. | 623/1.44 |
| 6,179,868 B1 | | 1/2001 | Burpee et al. | 623/1.17 |
| 6,183,505 B1 | * | 2/2001 | Mohn et al. | 623/1.11 |
| 6,221,042 B1 | | 4/2001 | Adams | 604/96.01 |
| 6,245,076 B1 | * | 6/2001 | Yan | 606/108 |
| 6,254,627 B1 | * | 7/2001 | Freidberg | 623/1.11 |

FOREIGN PATENT DOCUMENTS

| | | |
|---|---|---|
| WO | 96/26689 | 9/1996 |
| WO | 01/95833 A3 | 12/2001 |
| WO | 01/95833 A2 | 12/2001 |
| WO | 02/051490 A1 | 7/2002 |

OTHER PUBLICATIONS

U.S. Appl. No. 09/426,384, filed Oct. 25, 1999, Chen et al.
U.S. Appl. No. 09/668,496, filed Sep. 22, 2000, Yang.

* cited by examiner

*Primary Examiner*—Alvin Stewart
(74) *Attorney, Agent, or Firm*—Vidas, Arrett & Steinkraus PA

(57) ABSTRACT

A catheter for delivery of a prosthesis comprises an expandable member which includes a portion which foreshortens longitudinally upon radial expansion of the expandable member.

21 Claims, 6 Drawing Sheets

MATCHED BALLOON TO STENT SHORTENING

BACKGROUND OF THE INVENTION

Balloons and stents for delivery in a bodily vessel are typically matched in length when the balloon is in the uninflated state and the stent is unexpanded. During deployment of the stent, the stent typically shortens and the balloon grows in length. This can result in unnecessary trauma to healthy portions of a bodily vessel as the balloon applies a force to portions of the vessel which do not require stenting.

It would be desirable to provide a balloon and stent which are substantially the same length in the unexpanded state and which, to the extent they foreshorten, are characterized by similar foreshortening rates. It is expected that by matching the length of the stent and the balloon and by matching the foreshortening rates of the two, restenosis may be reduced by reducing the extent to which healthy regions of a vessel are subject to dilation.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, the invention is directed to a catheter comprising an expandable member including a portion which foreshortens longitudinally upon radial expansion. The expandable member may comprise a foreshortening balloon and/or a foreshortening belt. Where the expandable member comprises a balloon, a prosthetic device, for example a stent, may optionally be disposed about the balloon. Desirably, where the prosthetic device foreshortens on expansion, the balloon is characterized by a foreshortening rate $R_b$ and the prosthetic device is characterized by a foreshortening rate $R_p$ substantially equal to $R_b$. Also desirably, the balloon includes a body portion which is substantially the same length as the optional prosthetic device.

Where the expandable member comprises at least one belt which foreshortens, desirably a prosthetic device such as a stent is disposed about the belt. More desirably, where the belt is characterized by a foreshortening rate $R_b$ and the prosthetic device is characterized by a foreshortening rate $R_p$, $R_p$ is substantially equal to $R_b$. Optionally, the belt may be disposed about the circumference of a balloon. A single belt may be provided or a plurality of belts may be provided. Where a single belt is provided, desirably, the belt and the prosthetic device are substantially the same length. Where a multiplicity of belts are provided, at least some of the belts are characterized by a foreshortening rate $R_b$, and the prosthetic device is characterized by a foreshortening rate $R_p$ substantially equal to $R_b$. Desirably, the belts do not extend beyond the prosthetic device. Optionally, the belt may be in the form of a braid or a coil.

In another embodiment, the invention is directed to a catheter for delivering an implantable prosthetic device to a desired location in a bodily vessel comprising an expandable member and a prosthetic device disposed about the expandable member. The expandable member includes a portion which changes in length in tandem with the prosthetic device. Desirably, the implantable prosthetic device is a stent and the expandable member comprises a balloon. The expandable member is capable of lengthening at a rate of $R_b$ and the stent is capable of lengthening at a rate $R_s$ substantially equal to $R_b$.

In another embodiment, the invention is directed to a method of preparing a prosthesis delivery catheter comprising the steps of selecting a prosthesis, the prosthesis characterized by a foreshortening rate $R_p$, selecting a catheter comprising an expandable member including a portion which foreshortens longitudinally upon radial expansion and disposing the prosthesis about the expandable member. Desirably, the prosthesis is a stent and the expandable member comprises a balloon which foreshortens at a rate $R_b$ substantially equally to $R_p$. Where the expandable member comprises a belt, the prosthesis is disposed about the belt in the disposing step. Desirably, the prosthesis and the belt are substantially the same length. Also desirably, belt foreshortens at a rate $R_b$ substantially equally to $R_p$.

In yet another embodiment of the inventive method, the prosthesis is a stent and the method involves the step of selecting the catheter and the stent so that the foreshortening rate of the stent is equal to the foreshortening rate of the portion of expandable member which foreshortens on expansion.

Additional details and/or embodiments of the invention are discussed below.

BRIEF DESCRIPTION OF THE SEVERAL VIEWS OF THE DRAWING(S)

DETAILED DESCRIPTION OF THE INVENTION

Figure 1:
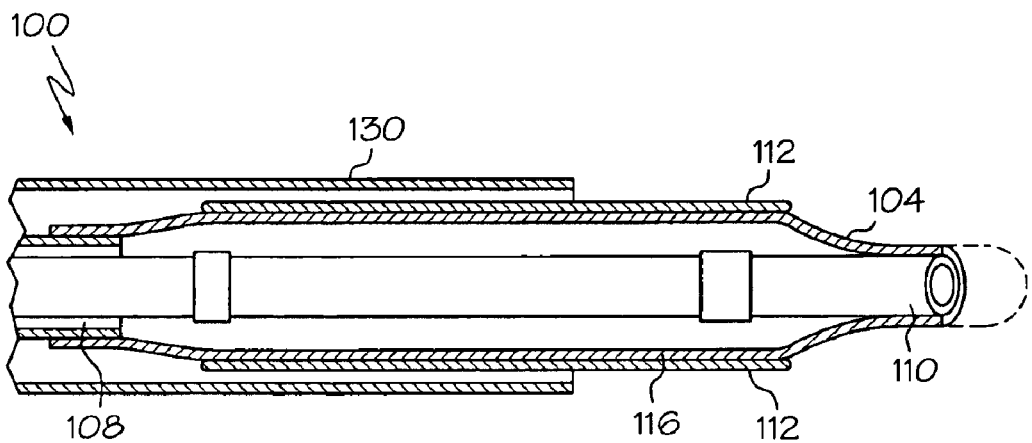
FIG. 1 is a side profile section showing an inventive balloon and stent.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, like reference numerals in the figures shall refer to like features unless otherwise indicated.

Also for the purposes of this disclosure, the stent foreshortening rate $R_s$ is defined as the ratio of the change in length of the stent to the change in diameter of the stent. The prosthesis foreshortening rate $R_p$ is defined as the ratio of the change in length of the prosthesis to the change in diameter of the prosthesis. Similarly, the foreshortening rate $R_b$ of the portion of the expandable member which foreshortens is defined as the ratio of the change in length of the portion of the expandable member to the change in diameter of the portion of the expandable. For example, where the expandable member is a balloon, $R_b$ is the ratio of the change in balloon length to the change in balloon diameter on expansion of the balloon.

Figure 2:
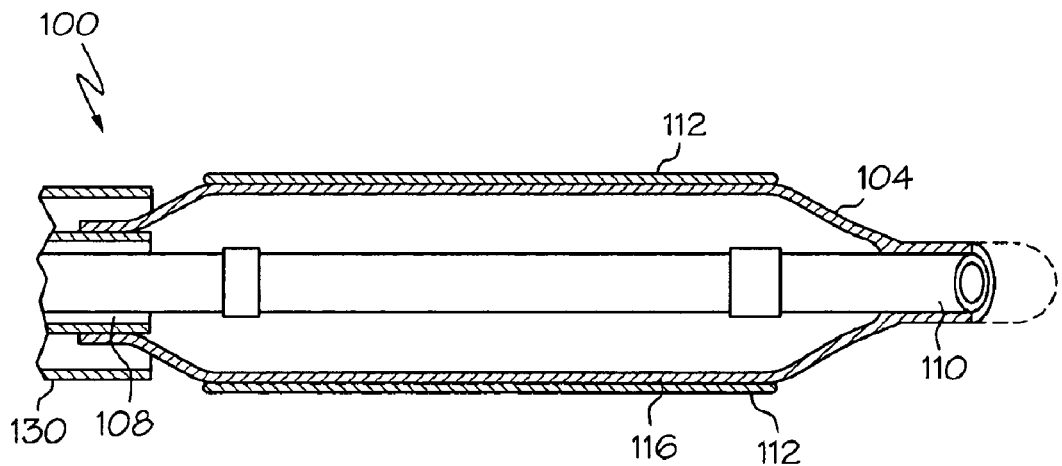
FIG. 2 is a side profile section, similar to FIG. 1, with the balloon and the stent fully inflated to deployment diameter.

The invention is directed in one embodiment to a catheter comprising an expandable member including a portion which foreshortens longitudinally upon radial expansion. As shown in FIGS. 1 and 2, distal end of catheter 100 includes an expandable member in the form of balloon 104. In FIG. 1, balloon 104 is shown in the uninflated state while in FIG. 2, balloon 104 is shown inflated. The proximal end of the catheter is not shown. Balloon 104 is supplied with an inflation fluid via inflation lumen 108. Balloon 104 is disposed about inner member tube 110. Desirably, inner member 110 is in the form of a tube. An optional retractable outer tube 130 may also be provided.

The invention also contemplates other types of expansion members. Examples of suitable catheters with an expansion member which may be modified for use in the present invention are described in U.S. Pat. No. 5,772,669 and U.S. Pat. No. 6,036,697.

Desirably, an optional prosthetic device is disposed about the balloon. As shown in FIGS. 1 and 2, the prosthetic device is stent 112. Stent 112 desirably is a balloon or otherwise mechanically expandable stent. Stent 112 may also be self-expanding, or a hybrid self-expanding in-part and mechanically expandable in part. Examples of self-expanding stents and balloon expandable stents are provided in WO 9626689 and in U.S. Pat. No. 5,972,018.The term stent is also intended to include stent-grafts and other grafts. Other types of prosthetic devices which may be used include vena cava filters.

Where a stent is used and the stent foreshortens on expansion at a rate of $R_s$, and the balloon foreshortens at a rate $R_b$, desirably the stent foreshortening rate $R_s$ is substantially equal to $R_b$. Desirably body portion 116 of balloon 104 is substantially the same length as stent 112.

Figure 3:
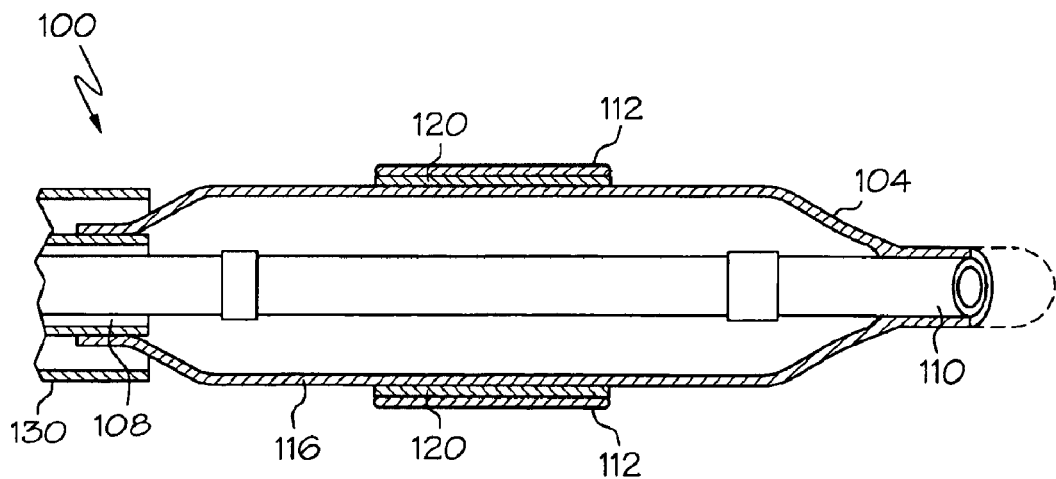
FIG. 3 is a side profile section, showing a balloon in combination with a belt and a stent, with the balloon partially inflated.

In another embodiment, as shown in FIG. 3, expandable member in the form of balloon 104 further comprises at least one belt 120 extending about the circumference of the balloon. Belt 120 foreshortens on radial expansion. Optionally, a prosthesis, desirably in the form of stent 112, is disposed about the belt. Belt 120 is characterized by a foreshortening rate $R_b$ and stent 112 is characterized by a foreshortening rate $R_s$. Desirably, $R_s$ is substantially equal to $R_b$. As shown in FIG. 3, only one belt is disposed about the balloon and stent 112 and belt 120 are, desirably, substantially the same length. Balloon 104 may be as long as belt 120 or longer. Catheter 100 is further shown with optional retractable outer tube 130.

Figure 4:
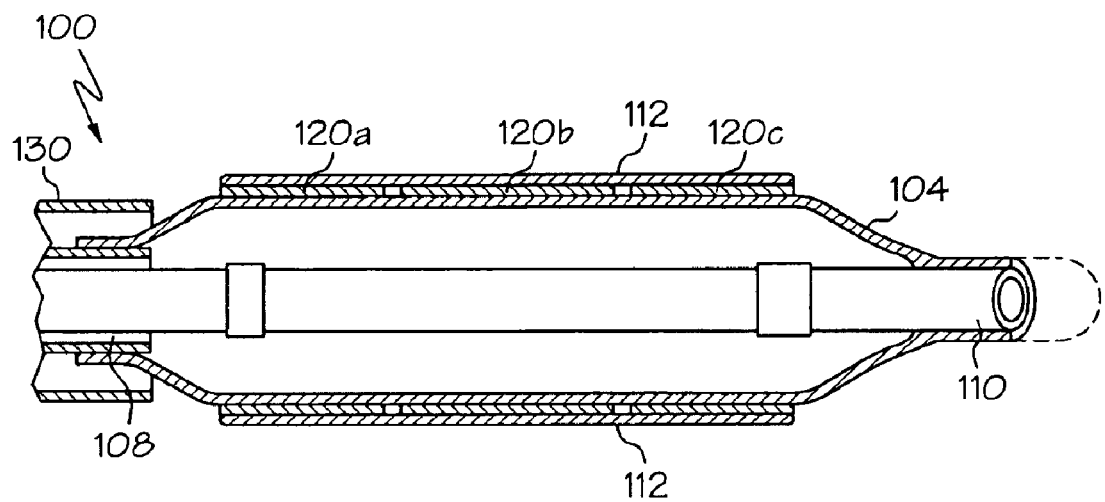
FIG. 4 is a side profile section, showing a balloon in combination with a plurality of belts and a stent, with the balloon partially inflated.

The invention also contemplates embodiments in which a plurality of belts 120a–c are provided, as shown in FIG. 4. Desirably, the belts do not extend beyond the stent. At least some of belts 120a–c are characterized by a foreshortening rate $R_b$, and the stent is characterized by a foreshortening rate $R_s$ which, desirably, is substantially equal to $R_b$. Desirably, at least the proximal most belt 120a and the distal most belt 120c foreshorten upon radial expansion. More desirably, all of the belts foreshorten upon radial expansion.

Belt 120 is constructed and arranged to foreshorten on radial expansion. Belt 120 may be made of any suitable material. Desirably, the belt is made of a polymeric material. An example of a suitable polymer for use in the belt is polyamide. Kevlar®, a family of aromatic polyamide available from DuPont, may also be used. Other suitable polymers include liquid crystal polymers (LCP's).

Figure 5:
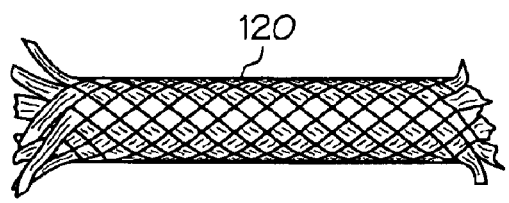
FIG. 5 is a side profile view of a braid.

In one variant, the belt is provided in the form of a braid, as shown at 120 in FIG. 5. The braid angle and the dimensions, including the width and diameter, of the individual members forming the braid may be varied so that the rate of foreshortening of the braid is equal to the foreshortening rate of the stent or other prosthesis. More generally, the pick rate of the braid may be chosen so that the rate of foreshortening of the braid is equal to the foreshortening rate of the stent or other prosthesis. Where a braided stent is used, the pick rate of the braid may equal the pick rate of the stent. As an example, a braid made of Kevlar® or LCP fibers may be used in conjunction with a slotted tube or braided stent.

Figure 6:
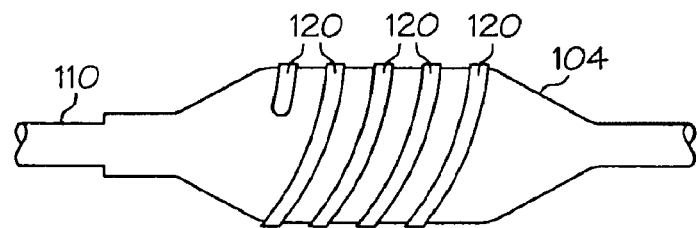
FIG. 6 is a schematic illustration of a balloon in combination with a belt in the form of a coil.

The belt may also be provided in the form of a coil as shown at 120 in FIG. 6. The coil may be made of suitable materials whether polymeric or otherwise. The pitch of the coil and the materials may be selected to achieve the desired foreshortening rate.

Figure 7:
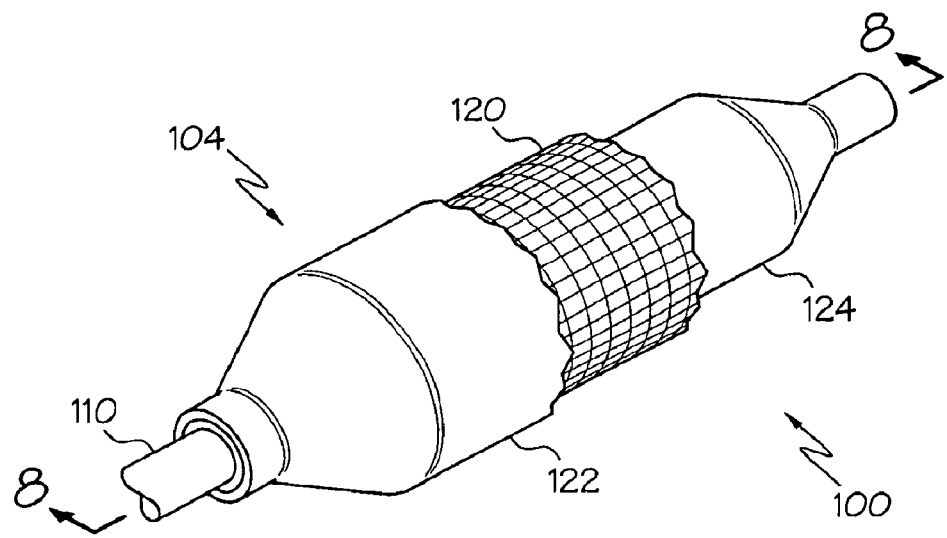
FIG. 7 is a perspective view of an inventive balloon and catheter with parts cut away.
Figure 8:
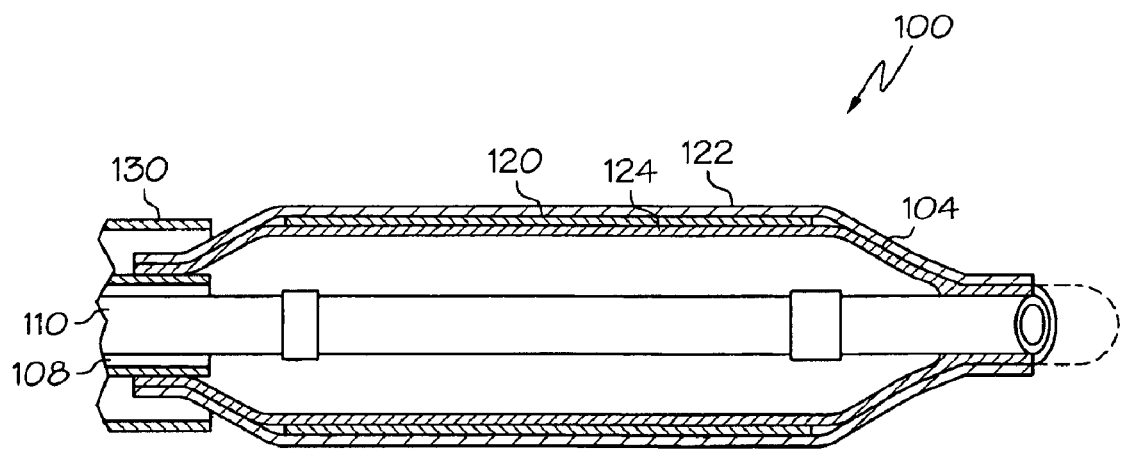
FIG. 8 is a cross-sectional view of an inventive balloon and catheter similar to that shown in FIG. 7.

In another embodiment of the invention, as shown in FIG. 7, balloon 104 includes an inner layer of material 124, belt 120 disposed about inner layer 124 and an outer layer of material 122. A portion of outer layer 122 and belt 120 have been cut away for illustrative purposes. Belt 120, as shown in FIG. 7, is in the form of a mesh. Belt 120 may optionally be in the form of a braid, a coil or any other suitable form which foreshortens upon inflation of the balloon. A cross-sectional view of a balloon catheter similar to that shown in FIG. 7, taken along line 8—8, is shown generally at 100 in FIG. 8. The balloon catheter shown in FIG. 8 further comprises an optional outer tube 130 disposed about inner member 110. Inner member 110 desirably is in the form of a tube. As shown in FIG. 8, the belt is limited to the body portion of the balloon. The invention also contemplates providing a belt which is coextensive with the inner and outer layers of the balloon extending the entire length of the balloon.

Whether the balloon is provided with one, two or more layers, it is also within the scope of the invention for the belt to be the same length as the length of the balloon.

Figure 9:
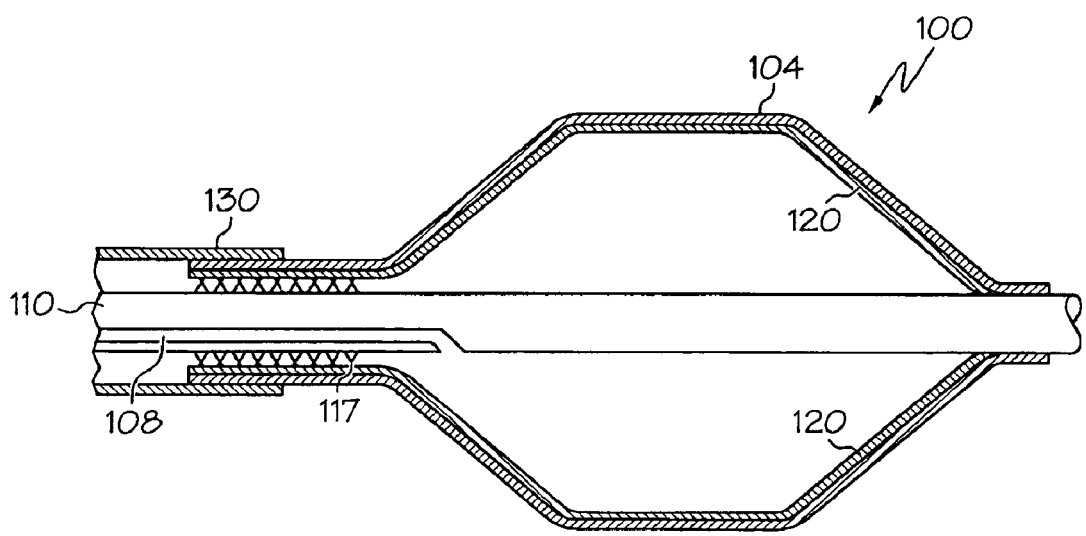
FIG. 9 is a cross-sectional view of another inventive balloon and catheter.

In yet another embodiment of the invention, as shown in FIG. 9, balloon 104 includes at least one and, desirably, a plurality of reinforcing members 120. Reinforcing members 120 may be in any suitable form including cords, fibers, filaments and braids. Balloon 104 is sealed to inner member 110 via sliding seal 117. Balloon 104 may be supplied with an inflation fluid via inflation lumen such as that shown at 108 by way of example. As balloon 104 is expanded radially outward, reinforcing members 120 shrink lengthwise and the balloon shrinks in length. Desirably, the balloon foreshortening rate $R_b$ is substantially equally to the foreshortening rate of a stent or other prosthesis (not shown) disposed thereabout.

The reinforcing members may be provided in a variety of ways including as an integral part of the balloon material, as an additional interior or exterior layer of the balloon, or in-between layers of balloon material.

The reinforcing members may be made of any suitable material including polyethyleneterephthalate (PET), polybutylene terephthalate (PBT), polytrimethylene terephthalate (PTT), Nylon™, engineering thermoplastic polyurethanes, fluoropolymers, polyester/polyether elastomers such as Arnitel™ available from DSM Engineering, polyurethane-polyether polymers, such as Tecothane™ 1055D or 1075D, Tecoplast™ 470 both of which are available from Thermedics, Inc.; polyester-polyurethanes, such as Estane™ 58170 sold by BF Goodrich; polyether block amides, such as Pebax™ 7233 or 6333 both of which are available from Elf Atochem. Other materials which may also be used include, but are not limited to: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, and any combinations thereof Additional details concerning the construction of balloons having fibers therein may be found in U.S. application Ser. No. 09/426,384.

Figure 10A:
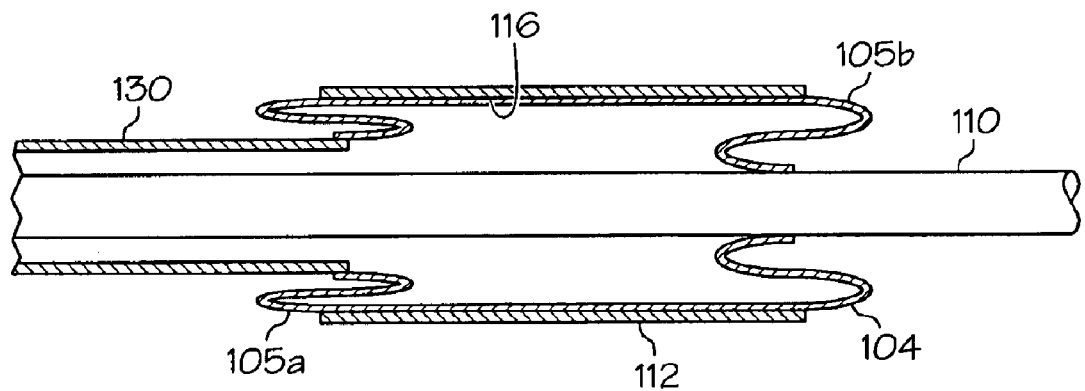
FIG. 10a is a cross-sectional view of another inventive balloon and catheter prior to inflation of the balloon.
Figure 10B:
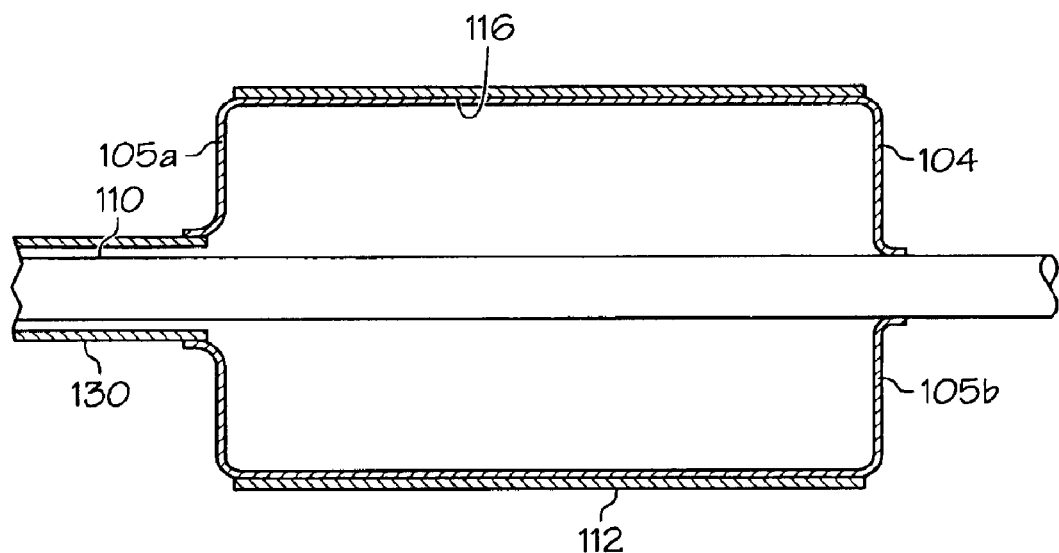
FIG. 10b is a cross-sectional view of another inventive balloon and catheter prior following inflation of the balloon.

Another inventive catheter for delivering a prosthetic device is shown generally at 100 in FIGS. 10a and 10b. Balloon 104 is disposed about inner member 110 and in fluid communication with inflation lumen 108. At least one and, desirably, as shown in FIG. 10a, both ends of balloon 104 include overhanging portions 105a and 105b. Overhanging portions 105a and 105b each form a double layer about the inner member. Proximal overhanging portion 105a extends in a proximal direction beyond the point or region of connection between the proximal end of the balloon and the inner member or any other catheter tube or member to which it may be joined. Distal overhanging portion 105b extends in a distal direction beyond the point or region of connection between the distal end of the balloon and the inner member any other catheter member to which it may be joined. Desirably, the length of the overhanging portions ranges from about 0.5 mm to about 2 mm. Prosthetic device 112, suitably a stent or any other prosthetic device disclosed herein, is optionally disposed about body portion 116 of balloon 104. Upon expansion of balloon 104, the one or more overhanging regions extend substantially radially outward and minimally overhang the inner member if at all. Desirably, the length of body portion 116 remains unchanged on expansion of the balloon or decreases in length by an amount corresponding to the decrease in length of the stent or other prosthesis during expansion.

Figure 11:
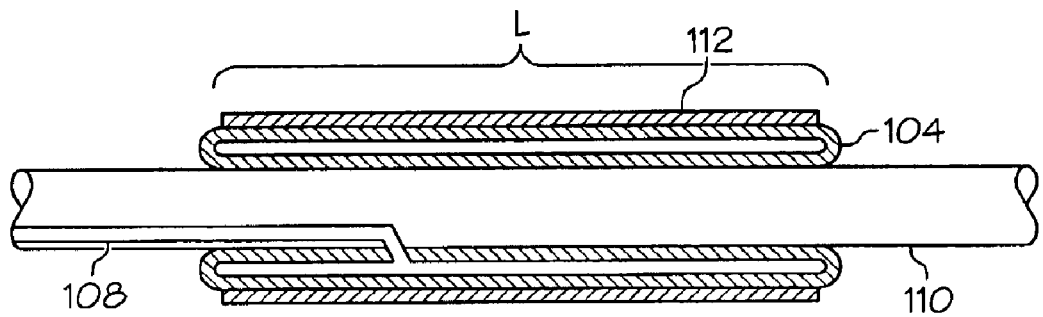
FIG. 11 is a cross-sectional view of an inventive toroidal balloon and catheter in an unexpanded configuration.

In yet another embodiment, the invention is directed to a toroidal medical balloon which foreshorten on expansion. Balloon 104, shown in an uninflated configuration in FIG. 11, is disposed about inner member 110. Balloon 104 is supplied with an inflation fluid via inflation lumen 108. As with any of the other embodiments disclosed herein, the invention also contemplates other arrangements of inflation lumens. For example, the inflation lumen could be internal to the inner member or could form a part of the inner member. The balloon may be made of expanded PTFE, elastomeric materials including latex or silicone or any other suitable balloon materials as known in the art including compliant balloon materials and non-compliant balloon materials. Examples of balloon materials are disclosed in U.S. Pat. Nos. 5,830,182 and U.S. Pat. No. 5,500,181.

Desirably, an optional prosthetic device is disposed about the balloon. Suitable prosthetic devices include stents and any of the other prosthetic devices disclosed herein. More desirably, where the prosthetic device foreshortens upon expansion, the rate of foreshortening of the prosthetic device and the balloon is matched. As shown in FIGS. 8 and 11, the foreshortening of stent 112 and balloon 104 is matched— stent 112 and balloon 104 foreshorten at an equal rate with both the balloon and the stent shrinking from a length L prior to expansion to a length L–ΔL following expansion.

Figure 12:
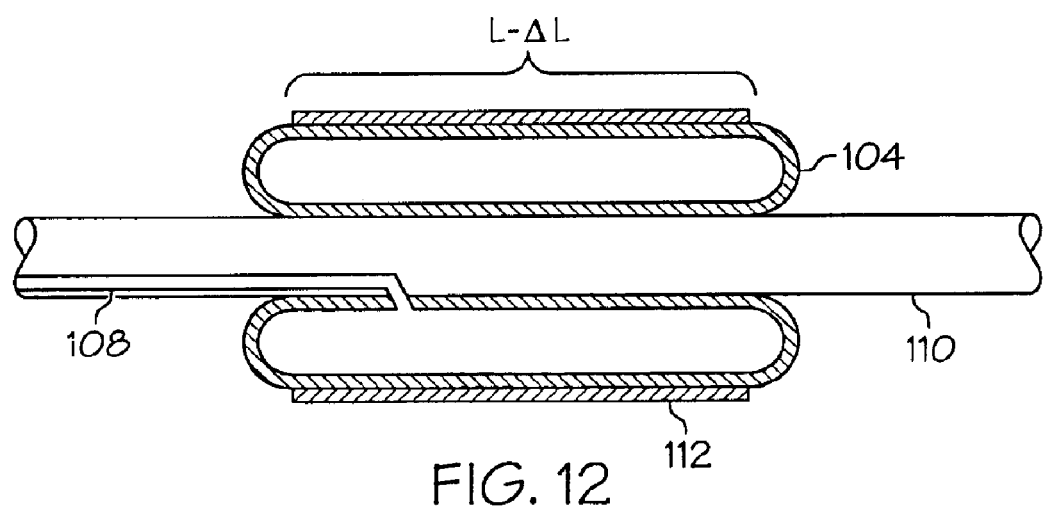
FIG. 12 is a cross-sectional view of an inventive toroidal balloon and catheter in an expanded configuration.

The arrangement of FIGS. 8 and 12 may further comprise a retractable sheath (not shown) disposed about the balloon as disclosed in U.S. Pat. No. 5,772,669 as well as other features of catheters as known in the art.

In another embodiment, the invention is directed to a catheter for delivering an implantable prosthetic device to a desired location in a bodily vessel comprising an expandable member and a prosthetic device disposed about the expandable member. The expandable member includes a portion which changes in length in tandem with the prosthetic device. Desirably, the implantable prosthetic device is a stent and the expandable member comprises a balloon. The expandable member is capable of lengthening at a rate of $R_b$, and the stent is capable of lengthening at a rate $R_s$ substantially equal to $R_b$. Any of the inventive catheters disclosed herein may be provided in such an embodiment. For example, in those embodiments in which a belt is provided, the belt may be constructed and arranged to lengthen at a rate equal to the rate at which the accompanying stent lengthens. Where the belt is in the form of a braid, the construction of the braid, including the pick rate may be modified to match the stent and belt lengthening rates. Lengthening of the stent may occur as the stent is tracked through tortuous vessels during delivery of the stent to a desired bodily location.

The invention is also directed to methods of producing the inventive medical balloons for catheters disclosed herein. In accordance with one inventive method, a mandrel is provided and a first layer of balloon material deposited on the mandrel. Any suitable balloon material may be used including Pebax, Nylon, polyethylene terephthalate (PET) or polyethylene. A braid may then be disposed about the first layer. The braid may be the same length as the first balloon material or shorter. Desirably, the length of the braid will correspond to the length of the body portion of the balloon to be formed. The braid may be made of any of the materials disclosed above. A second layer of balloon material is then disposed about the braid and the first layer of material to complete the balloon preform. The mandrel is then removed and the balloon blown under standard balloon blowing conditions as known in the art to form the inventive balloon.

In accordance with another embodiment of the invention, a tube may be extruded and a braid disposed about the tube. A heat shrink wrap, for example Teflon™ based, in conjunction with the application of heat, may be used to embed the braid in the tube. The tube may then be blown in accordance with techniques well known in the art.

The invention is also directed to catheters having other types of expandable members for expanding prostheses including stents in conjunction with one or more foreshortening belts disposed about the expandable member.

In accordance with the invention, any of the inventive balloons disclosed herein may be provided with or without a prosthetic device disposed thereabout.

In accordance with the invention, the inventive catheter may further comprise a sock at the proximal and/or distal end of the balloon or other expandable member to aid in retaining a stent or other prosthesis on the balloon or expandable member. The sock(s) may be made of any suitable material as known in the art. At least a portion of the sock may be radiopaque. More details concerning socks may be found in U.S. application Ser. No. 09/668,496.

The invention is directed, in another embodiment, to a method of preparing a prosthesis delivery catheter comprising the steps of selecting a prosthesis, the prosthesis characterized by a foreshortening rate $R_p$, selecting a catheter comprising an expandable member including a portion which foreshortens longitudinally upon radial expansion and disposing the prosthesis about the expandable member. The expandable member may comprise a balloon and/or a belt. Also desirably, the prosthesis is a stent. Any of the other prostheses disclosed above may also be used.

Where the expandable member comprises a balloon, desirably, the balloon foreshortens at a rate $R_b$ substantially equally to $R_p$. Where the expandable member comprises a belt, the prosthesis is disposed about the belt in the disposing step. Desirably, the belt and the prosthesis are substantially the same length. Also desirably, the belt foreshortens at a rate $R_b$ substantially equally to $R_p$.

The inventive methods may comprise the further step of selecting the prostheses and the catheter so that the foreshortening rate of the prostheses is equal to the foreshortening rate of the portion of expandable member which foreshortens on expansion.

The inventive catheters and methods may be used in delivering prostheses to any suitable bodily vessel including coronary, mesentery, peripheral, or cerebral vasculature, veins, the gastrointestinal tract, the biliary tract, the urethra, the trachea, hepatic shunts and fallopian tubes.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 6 may be taken as alternatively dependent on claim 3, or on claim 4; etc.).

This completes the description of the preferred and alternate embodiments of the invention. Those skilled in the art may recognize other equivalents to the specific embodiment described herein which equivalents are intended to be encompassed by the claims attached hereto.

What is claimed is:

1. A catheter for deploying an implantable prosthetic device at a desired location in a bodily vessel comprising an expandable member and a prosthetic device, wherein the prosthetic device is a stent, the expandable member comprising a balloon, the balloon having a first cone portion and a second cone portion, and at least one belt extending about the circumference of the balloon, the stent being disposed at least partially about the belt, the expandable member having a portion which foreshortens longitudinally upon radial expansion of the expandable member, the portion which foreshortens being longitudinally positioned between the first cone portion and the second cone portion and at least partially within the stent and the stent being disposed about the balloon, wherein the radial expansion of the expandable member is achieved by applying internal fluid pressure to the balloon and wherein the belt is characterized by a foreshortening rate $R_b$ and the stent is characterized by a foreshortening rate $R_s$.

2. The catheter of claim 1 wherein the stent foreshortens on expansion.

3. The catheter of claim 2 wherein the balloon is characterized by a foreshortening rate $R_b$ and the stent is characterized by a foreshortening rate $R_s$ substantially equal to $R_b$.

4. The catheter of claim 3 wherein the balloon includes a body portion which is substantially the same length as the stent.

5. The catheter of claim 4 comprising a multiplicity of belts, the stent disposed about the belts, the belts not extending beyond the stent, wherein at least some of the belts are characterized by a foreshortening rate $R_b$, and the stent is characterized by a foreshortening rate $R_s$, substantially equal to $R_b$.

6. The catheter of claim 5 wherein the belts do not extend beyond the stent.

7. The catheter of claim 1 wherein $R_s$ is substantially equal to $R_b$.

8. The catheter of claim 7 wherein only one belt is disposed about the balloon.

9. The catheter of claim 8 wherein the belt and the stent are substantially the same length.

10. The catheter of claim 7 wherein the belt is in the form of a braid.

11. The catheter of claim 1 wherein the expandable member comprises a balloon, the balloon comprising one or more overhanging portions in which the balloon forms a double layer about the inner tube.

12. The catheter of claim 1 wherein the balloon comprises one or more reinforcing members which extend in an axial direction.

13. The catheter of claim 12 wherein the expandable member is capable of lengthening at a rate of $R_b$ and the stent is capable of lengthening at a rate $R_s$, substantially equal to $R_b$.

14. The catheter of claim 1, wherein the portion which foreshortens is entirely between the first cone portion and the second cone portion.

15. The catheter of claim 1, the prosthetic device having a tubular shape, wherein the portion which foreshortens is at least partially within the tubular shape.

16. A catheter for delivering an implantable prosthetic device to a desired location in a bodily vessel comprising an expandable member, the expandable member comprising a balloon, and a prosthetic device disposed about the balloon, the expandable member including a portion which changes in length in tandem with the prosthetic device, wherein the portion of the balloon changes in length by applying internal fluid pressure to the expandable member, the portion which changes in length comprising a belt, the belt being at least partially about the balloon and at least partially within the prosthetic device and having a foreshortening rate $R_b$ when the balloon expands.

17. The catheter of claim 16 wherein the implantable prosthetic device is a stent.

18. The catheter of claim 16, the balloon having a first cone portion and a second cone portion, wherein the portion which changes in length is entirely between the first cone portion and the second cone portion.

19. The catheter of claim 16, the prosthetic device having a tubular shape, wherein the portion which changes is at least partially within the tubular shape.

20. A non-perfusion balloon comprising a balloon and a portion which foreshortens on expansion of the balloon, the portion which foreshortens comprising a belt about the balloon having a foreshorten rate $R_b$ when the balloon is expanded, wherein the expansion of the balloon is achieved by applying internal fluid pressure to the balloon, the balloon having a proximal cone portion and a distal cone portion, wherein the portion which foreshortens is at least partially centered between the distal cone portion and the proximal cone portion, the non-perfusion balloon further comprising a stent, wherein the stent is disposed about the balloon and the belt is at least partially between the stent and the balloon.

21. The non-perfusion ballon of claim 20, with a prostheic device disposed thereabout.

* * * * *